United States Patent
Gan et al.

(10) Patent No.: US 6,607,861 B2
(45) Date of Patent: Aug. 19, 2003

(54) APPLICATION OF γ-SVO AND MIXTURE OF γ-SVO/ε-SVO IN HIGH RATE ELECTROCHEMICAL LITHIUM CELLS CONTAINING SVO/CF$_x$/SVO SANDWICH CATHODES

(75) Inventors: Hong Gan, East Amherst, NY (US); Esther S. Takeuchi, East Amherst, NY (US)

(73) Assignee: Wilson Greatbatch Ltd., Clarence, NY (US)

(*) Notice: Subject to any disclaimer, the term of this patent is extended or adjusted under 35 U.S.C. 154(b) by 131 days.

(21) Appl. No.: 09/809,404

(22) Filed: Mar. 15, 2001

(65) Prior Publication Data

US 2001/0044047 A1 Nov. 22, 2001

Related U.S. Application Data (60) Provisional application No. 60/194,840, filed on Apr. 5, 2000.

(51) Int. Cl.$^7$ .................................................. H01M 4/34
(52) U.S. Cl. ................. 429/219; 429/213.5; 429/231.7; 429/245; 429/233; 429/231.9; 429/231.95; 429/332; 429/327
(58) Field of Search .............................. 429/219, 231.5, 429/231.7, 245, 233, 231.9, 231.95, 332, 327

(56) References Cited

U.S. PATENT DOCUMENTS

| | | | |
|---|---|---|---|
| 4,310,609 A | 1/1982 | Liang et al. ................. | 429/219 |
| 4,391,729 A | 7/1983 | Liang et al. ............. | 252/182.1 |
| 4,830,940 A | 5/1989 | Keister et al. ............... | 429/194 |
| 5,221,453 A | 6/1993 | Crespi ........................ | 204/291 |
| 5,389,472 A | 2/1995 | Takeuchi et al. ............. | 429/219 |
| 5,472,810 A | 12/1995 | Takeuchi et al. ............. | 429/219 |
| 5,498,494 A | 3/1996 | Takeuchi et al. ............. | 429/219 |
| 5,545,497 A | 8/1996 | Takeuchi et al. ............. | 429/219 |
| 5,558,680 A | 9/1996 | Takeuchi et al. ............. | 29/623.1 |
| 5,670,276 A | 9/1997 | Takeuchi et al. ............. | 429/219 |
| 5,695,892 A | 12/1997 | Leising et al. ............... | 429/219 |
| 5,811,206 A * | 9/1998 | Sunderland et al. ......... | 429/181 |
| 5,895,733 A | 4/1999 | Crespi et al. ................ | 429/219 |
| 5,902,696 A | 5/1999 | Smesko et al. | |
| 5,955,218 A | 9/1999 | Crespi et al. ................ | 429/219 |

FOREIGN PATENT DOCUMENTS

| | | | |
|---|---|---|---|
| EP | 0478303 A2 | 9/1991 | |
| EP | 532 313 A1 | 3/1993 | |
| EP | 0618630 A1 | 3/1993 | |
| EP | 0 689 256 A1 | 12/1995 | |
| EP | 0 849 225 A1 | 6/1998 | |

OTHER PUBLICATIONS

Abstract No. 125, Effect of Silver Content On The Performance of Primary Lithium/Silver Vanadium Oxide Batteries, E. S. Takeuchi and P. Keister.

Journal of Power Sources, 21 (1987) 133–141—Lithium/Silver Vanadium Oxide Batteries With Various Silver To Vanadium Ratios, Esther Sans Takeuchi and Pamela Piliero.

Solid–State Cathode Materials For Lithuim Batteries: Effect Of Synthesis Temperature on the Physical and Electrochemical Properties of Silver Vanadium Oxide, Randolph A. Leising and Esther Sans Takeuchi.

Solid–State Synthesis and Characterization of Silver Vanadium Oxide for Use as a Cathode Material for Lithium Batteries, Randolph A. Leising and Esther Sans Takeuchi.

* cited by examiner

*Primary Examiner*—Laura Weiner
(74) *Attorney, Agent, or Firm*—Michael F. Scalise (57) ABSTRACT

Lithium electrochemical cells having a sandwich cathode electrode of SVO/CF$_x$/SVO active materials are described. Such a design improves the service life of defibrillator electrochemical cells. A preferred formulation uses γ-SVO/CF$_x$/γ-SVO or (γ+ε)-SVO/CF$_x$/(γ+ε)-SVO sandwiched cathode electrodes.

18 Claims, 7 Drawing Sheets

APPLICATION OF γ-SVO AND MIXTURE OF γ-SVO/ε-SVO IN HIGH RATE ELECTROCHEMICAL LITHIUM CELLS CONTAINING SVO/CF$_x$/SVO SANDWICH CATHODES

CROSS-REFERENCE TO RELATED APPLICATION

This application claims priority based on provisional application Ser. No. 60/194,840, filed Apr. 5, 2000.

BACKGROUND OF THE INVENTION

1. Field of the Invention

The present invention generally relates to the conversion of chemical energy to electrical energy. More particularly, this invention relates to an application and design of a defibrillator battery and, more specifically, a high capacity lithium battery designed for high rate discharge applications.

2. Prior Art

Implantable ventricular cardiac defibrillators use lithium/silver vanadium oxide (Li/SVO) electrochemical cells as their power sources. For an implantable medical device, it is preferable that the device be as small as possible, responsive to the patient's medical needs, contribute to long device service life, and the like. Therefore, when batteries are built for these medical applications, special cell designs are needed to meet their requirements. For implantable cardiac defibrillator applications, one of the most important requirements is that the power source provide high energy (25 to 40 joules) within as short a period of time as possible, and preferably within 7 to 15 seconds, or less.

The relationship between delivered energy and the cell characteristics of voltage and current is:

$$\Delta E = V \times I \times t$$

where $\Delta E$ is the delivered energy (joules), V is the cell voltage under high current pulse discharge (Volt), I is the amplitude of the pulsing current (Ampere), and t is the high current pulsing time (second). In order to provide the desired energy ($\Delta E$) within a short time (t), the value of (V×I) needs to be kept as large as possible. Therefore, for an electrochemical cell designed to power an implantable cardiac defibrillator, the cell's internal resistance needs to be kept as low as possible, and at the same time the cell's voltage under high current pulsing needs to be maintained as high as possible.

In a traditional defibrillator cell, only silver vanadium oxide is used as the cathode active material. Silver vanadium oxide not only delivers sufficient energy needed under high current pulsing conditions, it also provides long service life. Therefore, other than the power capability (V×I), the capacity or energy density of a particular active material needs to be considered. Due to these reasons, ε-SVO ($Ag_2V_4O_{11}$) is a superior cathode active material for use in defibrillator cells due to its high volumetric capacity and acceptable power capability at all depths of discharge.

In U.S. application Ser. No. 09/560,060, filed Apr. 27, 2000, the disclosure of which is incorporated herein by reference, a double screen sandwich cathode design for defibrillator applications is described. In this invention, the cathode electrode has two different cathode active materials and two current collectors. The first cathode active material is sandwiched between the current collectors. This assembly is then sandwiched between two layers of the second cathode active material. One example of a sandwich cathode electrode design is CF$_x$ active material positioned between two layers of current collector screen which, in turn, are sandwiched between two layers of SVO cathode material.

U.S. provisional application Ser. No. 60/204,477, filed May 16, 2000, the disclosure of which is incorporated herein by reference, describes cathode active materials for cells having sandwich cathode electrodes. A preferred cell design has a sandwiched SVO/CF$_x$/SVO cathode. This cathode chemistry discharges in a very different manner in comparison to traditional Li/SVO defibrillator cells. In fact, the preferred SVO material for a traditional Li/SVO cell (ε-phase, $Ag_2V_4O_{11}$) is not necessarily the most optimum SVO material for sandwich cathode electrode designs.

Accordingly, the present invention is directed to the use of a low volumetric capacity SVO material (γ-phase SVO, $Ag_{1.6}V_4O_{10.8}$), instead of, or in addition to, the high volumetric capacity ε-phase SVO, in cells containing SVO/CF$_x$/SVO sandwich cathode electrodes. This results in a defibrillator cell with higher power capability and longer service life than known by the prior art. For a further discussion of the preparation of γ-SVO and ε-SVO materials, reference is drawn to U.S. application Ser. No. 09/793,246, filed Feb. 26, 2001, the disclosure of which is incorporated herein by reference.

SUMMARY OF THE INVENTION

The present invention is directed to lithium electrochemical cells having a sandwich cathode electrode of SVO/CF$_x$/SVO active materials. Such a design improves the service life of defibrillator electrochemical cells. A preferred formulation uses γ-SVO/CF$_x$/γ-SVO or (γ+ε)-SVO/CF$_x$/(γ+ε)-SVO sandwiched cathode electrodes.

These and other aspects of the present invention will become increasingly more apparent to those skilled in the art by reference to the following description and to the appended drawings.

DETAILED DESCRIPTION OF THE PREFERRED EMBODIMENTS

As used herein, the term "pulse" means a short burst of electrical current of a significantly greater amplitude than that of a pre-pulse current immediately prior to the pulse. A pulse train consists of at least two pulses of electrical current delivered in relatively short succession with or without open circuit rest between the pulses. An exemplary pulse train may consist of four 10 second pulses (15.0 mA/cm$^2$ to 35.0 mA/cm$^2$) with a 15 second rest between pulses. The pulse discharge parameter is per cathode surface area.

An implantable cardiac defibrillator is a device that requires a power source for a generally medium rate, constant resistance load component provided by circuits performing such functions as, for example, the heart sensing and pacing functions. From time-to-time, the cardiac defibrillator may require a generally high rate, pulse discharge load component that occurs, for example, during charging of a capacitor in the defibrillator for the purpose of delivering an electrical shock to the heart to heart tachyarrhythmias, the irregular, rapid heartbeats that can be fatal if left uncorrected.

An electrochemical cell that possesses sufficient energy density and discharge capacity required to meet the rigorous requirements of implantable medical devices, such as a cardiac defibrillator, comprises an anode of a metal selected from Groups IA, IIA and IIIB of the Periodic Table of the Elements. Such anode active materials include lithium, sodium, potassium, etc., and their alloys and intermetallic compounds including, for example, Li—Si, Li—Al, Li—B and Li—Si—B alloys and intermetallic compounds. The preferred anode comprises lithium. An alternate anode comprises a lithium alloy such as a lithium-aluminum alloy. The greater the amount of aluminum present by weight in the alloy, however, the lower the energy density of the cell.

The form of the anode may vary, but preferably the anode is a thin metal sheet or foil of the anode metal, pressed or rolled on a metallic anode current collector, i.e., preferably comprising titanium, titanium alloy or nickel, to form an anode component. Copper, tungsten and tantalum are also suitable materials for the anode current collector. In the exemplary cell of the present invention, the anode component has an extended tab or lead of the same material as the anode current collector, i.e., preferably nickel or titanium, integrally formed therewith such as by welding and contacted by a weld to a cell case of conductive metal in a case-negative electrical configuration. Alternatively, the anode may be formed in some other geometry, such as a bobbin shape, cylinder or pellet to allow an alternate low surface cell design.

The electrochemical cell of the present invention further comprises a cathode of electrically conductive material which serves as the other electrode of the cell. The cathode is preferably of solid materials and the electrochemical reaction at the cathode involves conversion of ions which migrate from the anode to the cathode into atomic or molecular forms. The solid cathode comprises a first active material formed by the chemical addition, reaction, or otherwise intimate contact of various metal oxides, preferably during thermal treatment, sol-gel formation, chemical vapor deposition or hydrothermal synthesis in mixed states. A preferred mixed metal oxide is silver vanadium oxide having the general formula $Ag_xV_2O_y$ in its γ-phase having in the general formula x=0.80 and y=5.4 and ε-phase having in the general formula x=1.0 and y=5.5, and combination and mixtures of phases thereof. For a more detailed description of such cathode active materials reference is made to U.S. Pat. No. 4,310,609 to Liang et al., which is assigned to the assignee of the present invention and incorporated herein by reference.

The sandwich cathode design of the present invention further includes a second active material of a relatively high energy density and a relatively low rate capability in comparison to the first cathode active material. The second active material is preferably a carbonaceous compound prepared from carbon and fluorine, which includes graphitic and nongraphitic forms of carbon, such as coke, charcoal or activated carbon. Fluorinated carbon is represented by the formula $(CF_x)_n$ wherein x varies between about 0.1 to 1.9 and preferably between about 0.5 and 1.2, and $(C_2F)_n$ wherein the n refers to the number of monomer units which can vary widely.

Before fabrication into a sandwich electrode for incorporation into an electrochemical cell according to the present invention, the first and second cathode active materials prepared as described above are preferably mixed with a binder material such as a powdered fluoro-polymer, more preferably powdered polytetrafluoroethylene or powdered polyvinylidene flouride present at about 1 to about 5 weight percent of the cathode mixture. Further, up to about 10 weight percent of a conductive diluent is preferably added to the cathode mixture to improve conductivity. Suitable materials for this purpose include acetylene black, carbon black and/or graphite or a metallic powder such as powdered nickel, aluminum, titanium and stainless steel. The preferred cathode active mixture thus includes a powdered fluoro-polymer binder present at about 3 weight percent, a conductive diluent present at about 3 weight percent and about 94 weight percent of the cathode active material.

Cathode components for incorporation into an electrochemical cell according to the present invention may be prepared by rolling, spreading or pressing the first and second cathode active materials onto a suitable current collector selected from the group consisting of stainless steel, titanium, tantalum, platinum, gold, aluminum, cobalt nickel alloys, nickel-containing alloys, highly alloyed ferritic stainless steel containing molybdenum and chromium, and nickel-, chromium- and molybdenum-containing alloys. The preferred current collector material is titanium, and most preferably the titanium cathode current collector has a thin layer of graphite/carbon material, iridium, iridium oxide or platinum applied thereto. Cathodes prepared as described above may be in the form of one or more plates operatively associated with at least one or more plates of anode material, or in the form of a strip wound with a corresponding strip of anode material in a structure similar to a "jellyroll".

According to the present invention, SVO cathode material, which provides a relatively high power or rate capability but a relatively low energy density or volumetric capacity, and $CF_x$ cathode material, which has a relatively high energy density but a relatively low rate capability, are individually pressed on opposite sides of a current collector screen, so that both materials are in direct contact with the current collector. Therefore, one exemplary cathode plate has the following configuration:

SVO/current collector/$CF_x$/current collector/SVO

An important aspect of the present invention is that the SVO material maintains direct contact with the current collector. Another important aspect of the present invention is that the $CF_x$ material never directly faces the lithium anode. In addition, the $CF_x$ material must be short circuited with the SVO material, either by direct contact or by parallel connection through the current collectors.

End of service life indication is the same as that of a standard Li/SVO cell. And, it has been determined that the SVO electrode material and the $CF_x$ electrode material according to the present invention reach end of life at the same time. This is the case in spite of the varied usage in actual defibrillator applications. Since both electrode materials reach end of service life at the same time, no energy capacity is wasted.

For Li/SVO cells, the running voltage is between 3.5 volts to 2.0 volts, depending on the depth of discharge (DOD). For Li/CF$_x$ cells, the running voltage is between 3.0 volts to 2.6 volts. Thus, when a lithium cell having a double screen sandwich cathode (SVO-screen-CF$_x$-screen-SVO) is discharged under a constant current or a constant resistance load, three discharge region are observed. In region 1: the SVO cathode is discharged first due to its higher running potential at the beginning of life (BOL>3.0V). In region 2: after the cell voltage drops to about 3.0 volts to about 2.6 volts, both the SVO and CF$_x$ materials are discharged at the same time. In region 3: when the voltage drops below about 2.6 volts, the CF$_x$ cathode material is fully discharged and the SVO material again provides the majority of power to the discharge current loads. Under high current pulse discharge conditions, the SVO material provides all of the power in regions 1 and 3. In region 2, the SVO material also provides all of the power under high current pulse discharge applications due to the lack of power capability of the CF$_x$ material. However, after each current pulse, the potential of the SVO material drops below that of the CF$_x$ material within the same sandwich cathode electrode. After each high current pulse, the CF$_x$ material recharges the SVO material until both have the same electrochemical potentials. From this, it is believed that when a lithium cell is discharged within region 2, both the SVO and CF$_x$ materials provide energy under low rate discharge conditions throughout the device service life. Furthermore, in this region only the SVO material provides energy under high current pulse discharge conditions.

Since CF$_x$ (x=1.1) cathode material (895.8 mAh/g, 2.42 Ah/ml) has a significantly higher theoretical capacity than that of SVO material (315.1 mAh/g, 1.37 Ah/ml for $\epsilon$-SVO), in order to obtain a cell with high capacity, the CF$_x$ layer within the sandwich cathode is kept as thick as possible at the expense of the SVO layer thickness. In such a case, the regions 1 and 3 capacities are decreased, and at the same time the region 2 capacity is increased. Therefore, the capacity of the SVO material in the sandwich cathode cell becomes less important, while its role of providing high power capability in discharge region 2 become more critical. For these reasons, the preferred cathode active material for providing high power capability is based on a candidate cathode active material's power capability in discharge region 2. The higher the power capability (larger value of V×I) of the cathode material at potentials of about 3.0 volts to about 2.6 volts, the more preferred the material is for use in lithium cells having sandwich cathode electrode designs.

According to the present invention, $\gamma$-SVO provides higher power capability and lower Rdc under high current pulsing applications than that of $\epsilon$-SVO in discharge region 2. Under high current pulsing applications, higher power is delivered by the sandwich cathode electrode cells of the present invention containing $\gamma$-SVO as one of the cathode active material components.

In order to prevent internal short circuit conditions, the sandwich cathode is separated from the Group IA, IIA or IIIB anode by a suitable separator material. The separator is of electrically insulative material, and the separator material also is chemically unreactive with the anode and cathode active materials and both chemically unreactive with and insoluble in the electrolyte. In addition, the separator material has a degree of porosity sufficient to allow flow there through of the electrolyte during the electrochemical reaction of the cell. Illustrative separator materials include fabrics woven from fluoropolymeric fibers including polyvinylidine fluoride, polyethylenetetrafluoroethylene, and polyethylenechlorotrifluoroethylene used either alone or laminated with a fluoropolymeric microporous film, nonwoven glass, polypropylene, polyethylene, glass fiber materials, ceramics, polytetrafluoroethylene membrane commercially available under the designation ZITEX (Chemplast Inc.), polypropylene membrane commercially available under the designation CELGARD (Celanese Plastic Company, Inc.) and a membrane commercially available under the designation DEXIGLAS (C. H. Dexter, Div., Dexter Corp.).

The electrochemical cell of the present invention further includes a nonaqueous, ionically conductive electrolyte which serves as a medium for migration of ions between the anode and the cathode electrodes during the electrochemical reactions of the cell. The electrochemical reaction at the electrodes involves conversion of ions in atomic or molecular forms which migrate from the anode to the cathode. Thus, nonaqueous electrolytes suitable for the present invention are substantially inert to the anode and cathode materials, and they exhibit those physical properties necessary for ionic transport, namely, low viscosity, low surface tension and wettability.

A suitable electrolyte has an inorganic, ionically conductive salt dissolved in a nonaqueous solvent, and more preferably, the electrolyte includes an ionizable alkali metal salt dissolved in a mixture of aprotic organic solvents comprising a low viscosity solvent and a high permittivity solvent. The inorganic, ionically conductive salt serves as the vehicle for migration of the anode ions to intercalate or react with the cathode active material. Preferably, the ion forming alkali metal salt is similar to the alkali metal comprising the anode.

In the case of an anode comprising lithium, the alkali metal salt of the electrolyte is a lithium based salt. Known lithium salts that are useful as a vehicle for transport of alkali metal ions from the anode to the cathode include LiPF$_6$, LiBF$_4$, LiAsF$_6$, LiSbF$_6$, LiClO$_4$, LiAlCl$_4$, LiGaCl$_4$, LiC(SO$_2$CF$_3$)$_3$, LiN(SO$_2$CF$_3$)$_2$, LiSCN, LiO$_3$SCF$_3$, LiC$_6$F$_5$SO$_3$, LiO$_2$CCF$_3$, LiSO$_6$F, LiB(C$_6$H$_5$)$_4$ and LiCF$_3$SO$_3$, and mixtures thereof.

Low viscosity solvents useful with the present invention include esters, linear and cyclic ethers and dialkyl carbonates such as tetrahydrofuran (THF), methyl acetate (MA), diglyme, triglyme, tetragylme, dimethyl carbonate (DMC), 1,2-dimethoxyethane (DME), 1,2-diethoxyethane (DEE), 1-ethoxy,2-methoxyethane (EME), ethyl methyl carbonate, methyl propyl carbonate, ethyl propyl carbonate, diethyl carbonate, dipropyl carbonate, and mixtures thereof, and high permittivity solvents include cyclic carbonates, cyclic esters and cyclic amides such as propylene carbonate (PC), ethylene carbonate (EC), butylene carbonate, acetonitrile, dimethyl sulfoxide, dimethyl, formamide, dimethyl acetamide, $\gamma$-valerolactone, $\gamma$-butyrolactone (GBL), N-methyl-pyrrolidinone (NMP) and mixtures thereof. In the present invention, the preferred anode is lithium metal and the preferred electrolyte is 0.8M to 1.5M LiAsF$_6$ or LiPF$_6$ dissolved in a 50:50 mixture, by volume, of propylene carbonate as the preferred high permittivity solvent and 1,2-dimethoxyethane as the preferred low viscosity solvent.

The assembly of the electrochemical cells described herein is preferably in the form of a wound element configuration. That is, the fabricated negative electrode, positive electrode and separator are wound together in a "jellyroll" type configuration or "wound element cell stack" such that the negative electrode is on the outside of the roll to make electrical contact with the cell case in a case-negative configuration. Using suitable top and bottom insulators, the wound cell stack is inserted into a metallic case of a suitable size dimension. The metallic case may comprise materials such as stainless steel, mild steel, nickel-plated mild steel, titanium, tantalum or aluminum, but not limited thereto, so long as the metallic material is compatible for use with components of the cell.

The cell header comprises a metallic disc-shaped body with a first hole to accommodate a glass-to-metal seal/terminal pin feedthrough and a second hole for electrolyte filling. The glass used is of a corrosion resistant type having up to about 50% by weight silicon such as CABAL 12, TA 23, FUSITE 425 or FUSITE 435. The positive terminal pin feedthrough preferably comprises titanium although molybdenum, aluminum, nickel alloy, or stainless steel can also be used. The cell header is typically of a material similar to that of the case. The positive terminal pin supported in the glass-to-metal seal is, in turn, supported by the header, which is welded to the case containing the electrode stack. The cell is thereafter filled with the electrolyte solution described hereinabove and hermetically sealed such as by close-welding a stainless steel ball over the fill hole, but not limited thereto.

The above assembly describes a case-negative cell. As is well known to those skilled in the art, the electrochemical systems of the present invention can also be constructed in case-positive configurations.

The following examples describe the manner and process of an electrochemical cell according to the present invention, and they set forth the best mode contemplated by the inventors of carrying out the invention, but they are not to be construed as limiting.

EXAMPLE I

Discharge Voltage Profile of Cells with SVO/CF$_x$ Sandwich Cathode

Five cells were built containing anode electrodes of lithium metal pressed onto a nickel current collector screen. Cathodes were built having cathode active materials pressed onto two layers of titanium current collector screen to provide an electrode configuration of SVO-screen-CF$_x$-screen-SVO. The SVO material used was ε-phase SVO with a stoichiometry formula of $Ag_2V_4O_{11}$. A prismatic cell stack assembly configuration with two layers of microporous membrane polypropylene separator sandwiched between the anode and cathode electrodes was prepared. The electrode assembly was then hermetically sealed in a stainless steel casing in a case negative configuration and activated with an electrolyte of 1.0M LiAsF$_6$+0.05M DBC/PC:DME=1:1 (DBC=dibenzyl carbonate). The theoretical capacity of the cells was 2.645 Ah.

Test 1: Accelerated Pulse Train Test (APT)

Figure 1:
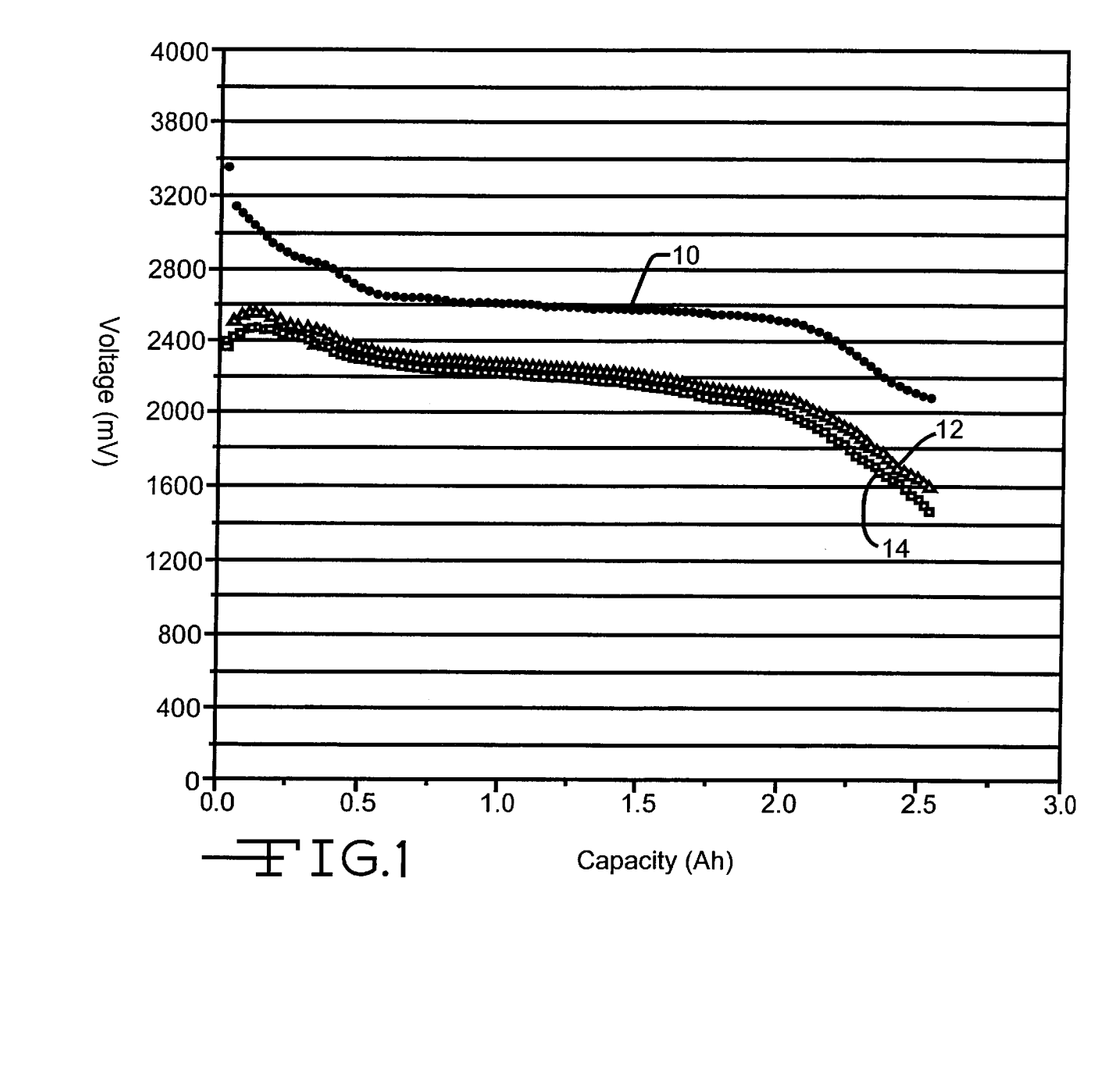
FIG. 1 is a graph constructed from the pulse discharge of a lithium cell having a sandwich cathode electrode of ε-SVO/CF$_x$/ε-SVO.

One of the cells built according to this example was accelerated pulse train discharged. This discharge regime consisted of the application of pulse trains of four 10 second, 2 amperes current pulses with a 15 second rest between pulses applied every 30 minutes. The voltage profiles of pre-pulse potentials (curve 10), pulse 1 minimum potentials (curve 12) and pulse 4 minimum potentials (curve 14) are shown in FIG. 1. A voltage plateau at about 2.6V is clearly observed between 500 mAh to 1750 mAh. This voltage plateau is attributed to the CF$_x$ electrode [region 2]. Since the accelerated pulse discharge test is a relatively quick test (it takes only about 2.5 days to complete), the cathode voltages, especially for the CF$_x$ active material, were polarized.

Test 2: Slow Discharge Test at BOL

Three of the cells built according to this example were acceptance pulse train tested. This served to deplete the cells of approximately 1% of their theoretical capacity. Then, the cells were discharged under a 15.1 kΩ load interrupted every 39 days by pulse trains consisting four 10 second, 2 amperes current pulses with a 15 second rest between pulses. Data from the first two pulse trains (average of three cells) is summarized in Table 1.

TABLE 1

| Pulse Train | % DOD | Pprel (V) | V-Delay (V) | P1 min (V) | P4 min (V) |
|---|---|---|---|---|---|
| 1 | 1.01 | 3.214 | 0.000 | 2.495 | 2.443 |
| 2 | 7.49 | 3.091 | 0.000 | 2.536 | 2.419 |

The data in Table 1 illustrates that at BOL [region 1 at>3.0V], the cell voltage profiles follow that of a typical Li/SVO cells.

Test 3: Slow Discharge Test at MOL

One of the cells built according to this example was pre-discharged to about 50% DOD by following the APT test regime of Test 1. Then, the cell was discharged under a 15.1 kΩ load interrupted every 39 days by pulse trains consisting of four 10 second, 2 amperes current pulses with a 15 second rest between pulses. Data from the first two pulse trains is summarized in Table 2.

TABLE 2

| Pulse Train | % DOD | Pprel (V) | V-Delay (V) | P1 min (V) | P4 min (V) |
|---|---|---|---|---|---|
| 1 | 51.40 | 2.830 | 0.000 | 2.488 | 2.410 |
| 2 | 57.23 | 2.744 | 0.000 | 2.390 | 2.351 |

The data in Table 2 illustrates that at MOL [region 2] between about 3.0V to about 2.6V, the cell discharge background voltage profile follows that of a typical Li/CF$_x$ cell while the cell is still capable of providing the high current power typical of Li/SVO cells.

The results in this example demonstrate the discharge characteristics of three voltage profile regions for cells with SVO-screen-CF$_x$-screen-SVO sandwich cathodes. The region (2) discharge provides more than half of the total capacity of the cells having these sandwich cathode electrodes.

EXAMPLE II

Rdc and Power Capability Comparison of ε-SVO with γ-SVO

Figure 2:
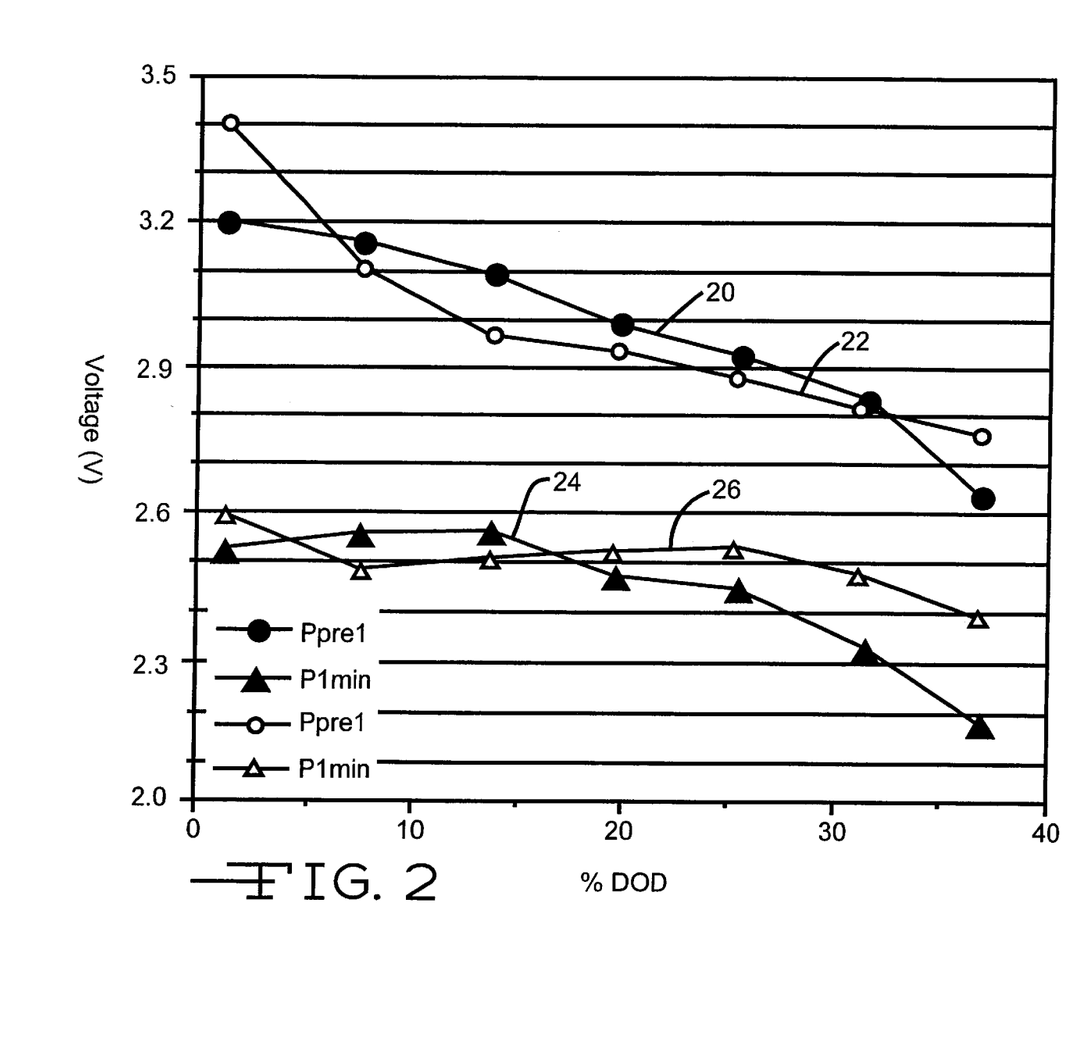
FIG. 2 is a graph constructed from the average prepulse voltages and pulse 1 minimum voltages of two groups of lithium cells, one having a cathode electrode of ε-SVO, the other of a γ-SVO material, discharged through seven pulse trains.
Figure 3:
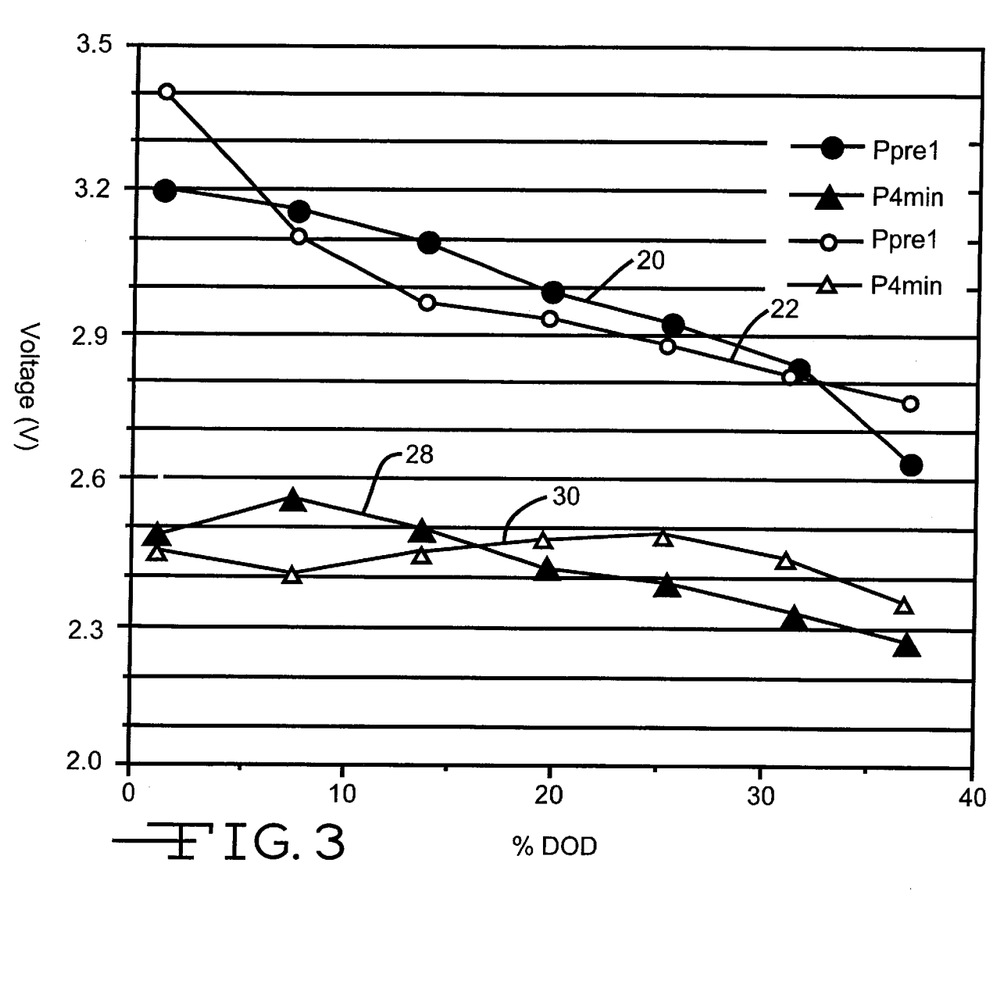
FIG. 3 is a graph constructed from a comparison of the average prepulse voltages and pulse 4 minimum voltages for the two cell groups used to construct the graph of FIG. 2.
Figure 4:
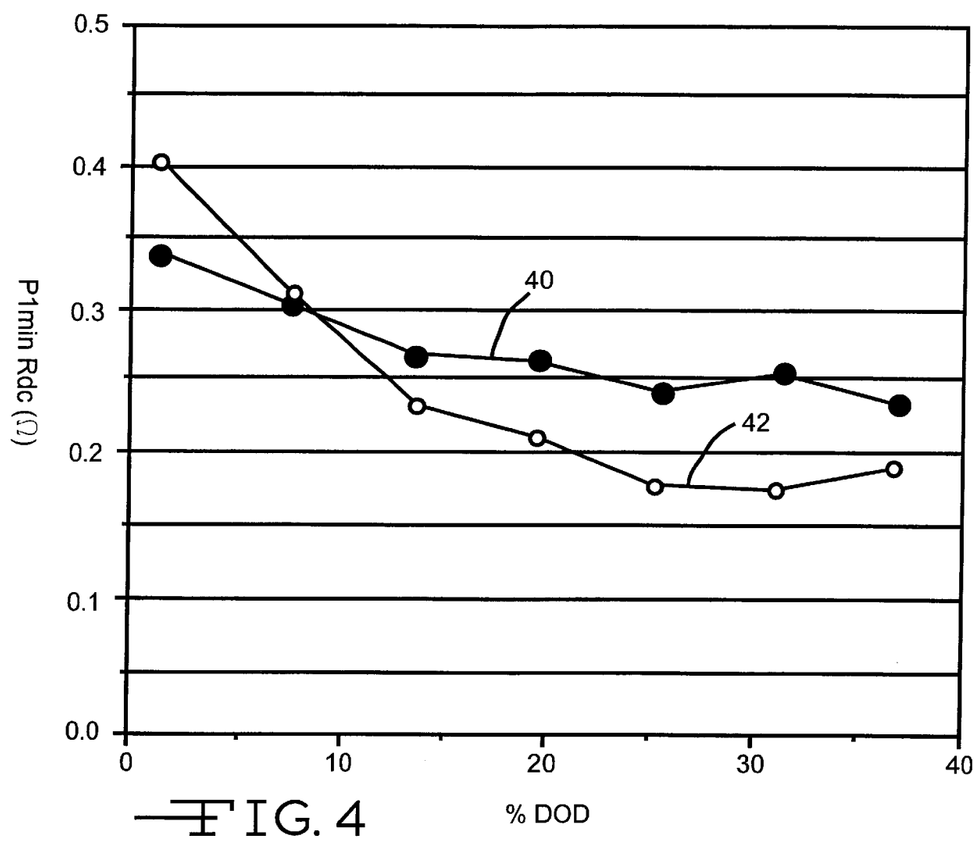
FIG. 4 is a graph constructed from the Rdc of the two cell groups used to construct the graph of FIG. 2.
Figure 5:
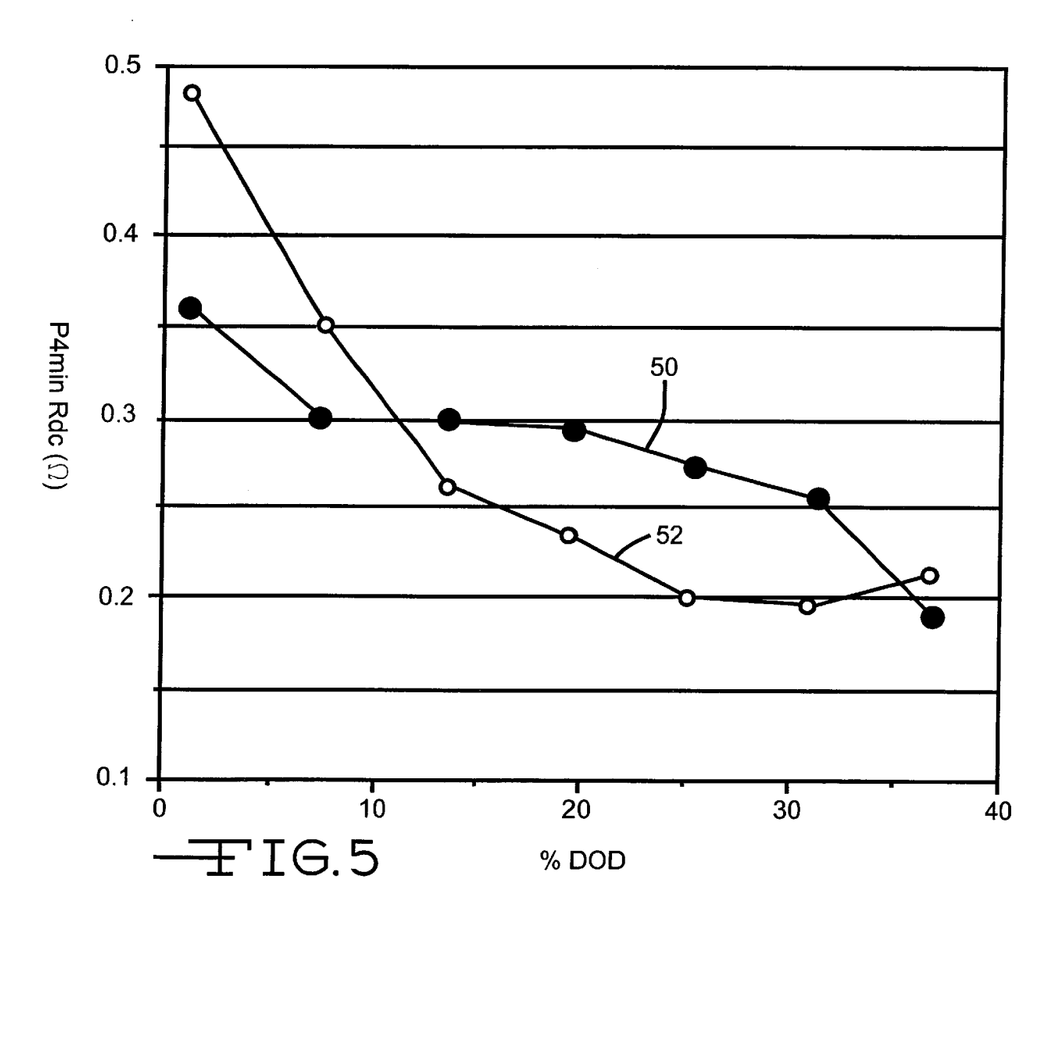
FIG. 5 is a graph constructed from the Rdc of the two cell groups used to construct the graph of FIG. 3.

Six cells were constructed in a similar manner as those described in Example I except that the cathodes were constructed in the configuration of SVO-screen-SVO and for the stoichiometry of the SVO material. In particular, three cells were built with ε-SVO having a stoichiometry formula of $Ag_2V_4O_{11}$ (group 1) and three cells were constructed with γ-SVO having a stoichiometry formula of $Ag_{1.6}V_4O_{10.8}$ (group 2). After burn-in and acceptance pulse train testing, these cells were discharged under a 22.1 kΩ load interrupted every 36 days by pulse trains consisting of four 10 second pulses having a cathode current density of 22.2 mA/cm$^2$ with a 15 second rest between pulses. The average pulse train data of the initial 7 pulse trains is summarized in FIG. 2 (P1min. comparison) and in FIG. 3 (P4min. comparison). In particular, curves 20 and 22 in FIGS. 2 and 3 are the respective prepulse voltages for the groups 1 and 2 cells, curves 24 and 26 in FIG. 2 are of the pulse 1 minimum voltages and curves 28 and 30 in FIG. 3 are of the pulse 4 minimum voltages of the respective groups 1 and 2 cells. The Rdc of the P1min. and the P4min. voltages for all pulse trains for the respective cell groups 1 and 2 were calculated and the results are illustrated in FIGS. 4 (curves 40 and 42) and 5 (curves 50 and 52).

For the group 1 cells with ε-SVO, the region 1 discharge is from 0% to about 20% DOD (background potentials>3.0V) while the region 2 discharge spans from about 20% DOD to about 35% DOD (3.0V>background potentials>2.6V). For the group 2 cells with γ-SVO, the region 1 discharge is from 0% to about 12% DOD (background potentials>3.0V) while the region 2 discharge spans from about 12% DOD to about 40% DOD (3.0V >background potentials>2.6V). Discharge region 2 can be divided into three voltage ranges: (a) 3.0V to 2.9V, (b) 2.9V to 2.8V, (c) 2.8V to 2.6V. The pulse minimum potentials of the group 2 cells were higher than those of the group 1 cells in all three voltage ranges, as shown in FIGS. 2 and 3. These results indicate that lithium cells having cathode electrodes with γ-SVO exhibit higher power capability than lithium cells having cathode electrodes with ε-SVO at region 2 discharge. The beneficial effect is further supported by the Rdc data shown in FIGS. 4 and 5. Within the region 2 discharge, the group 2 cells exhibited a lower Rdc than that of the group 1 cells throughout this region. Therefore, in this discharge region, less energy is wasted as heat due to the internal resistance for the group 2 cells than for the group 1 cells.

The results in Example II demonstrate the advantage of using γ-SVO over ε-SVO in a region 2 discharge in terms of higher pulse minimum potentials and lower Rdc in a lithium cell. Accordingly, for the reasons described herein above in the detailed description, it is preferred to use γ-SVO ($Ag_{1.6}V_4O_{10.8}$) instead of ε-SVO ($Ag_2V_4O_{11}$) in sandwich cathode defibrillator cells as described in Example I.

EXAMPLE III

Rdc and Power Capability Comparison of ε-SVO with (γ+ε)-SVO

Figure 6:
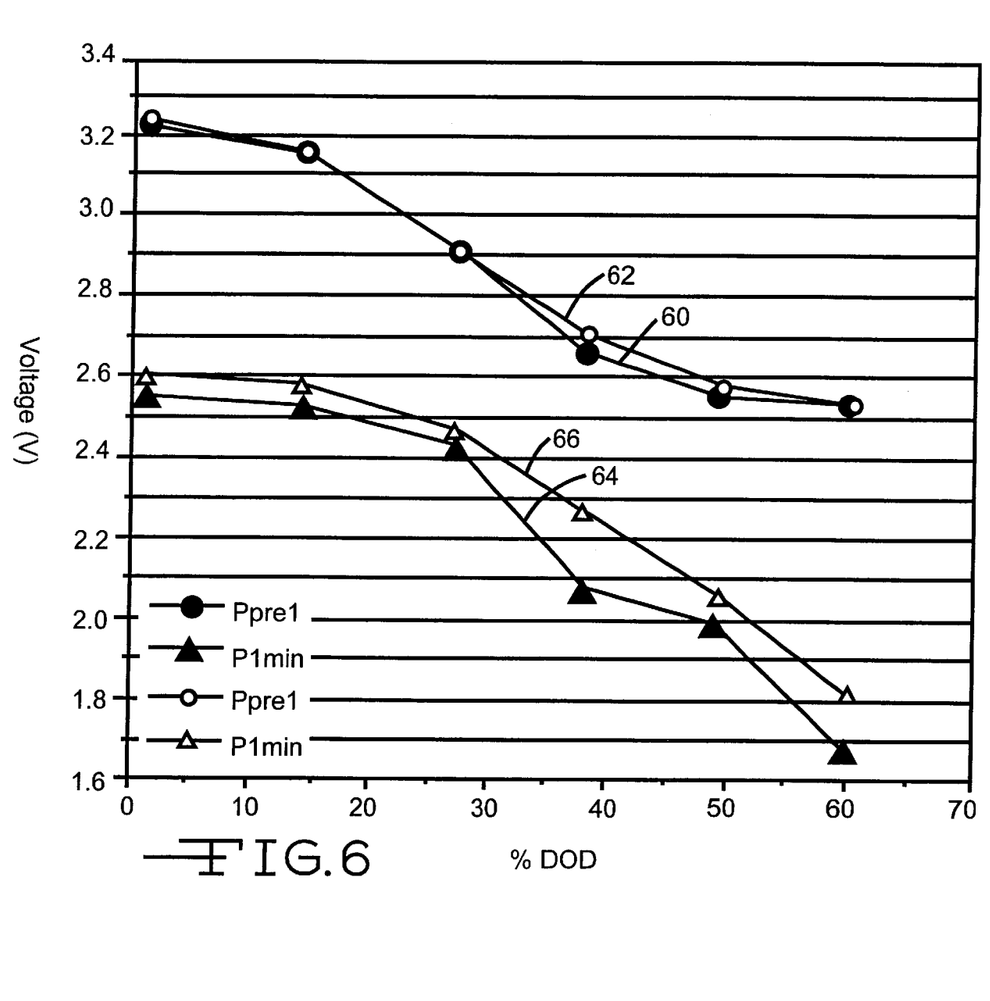
FIG. 6 is a graph constructed from the average prepulse voltages and pulse 1 minimum voltages of two groups of lithium cells, one having a cathode electrode of ε-SVO, the other of a γ-SVO and ε-SVO design, discharged through six pulse trains.
Figure 7:
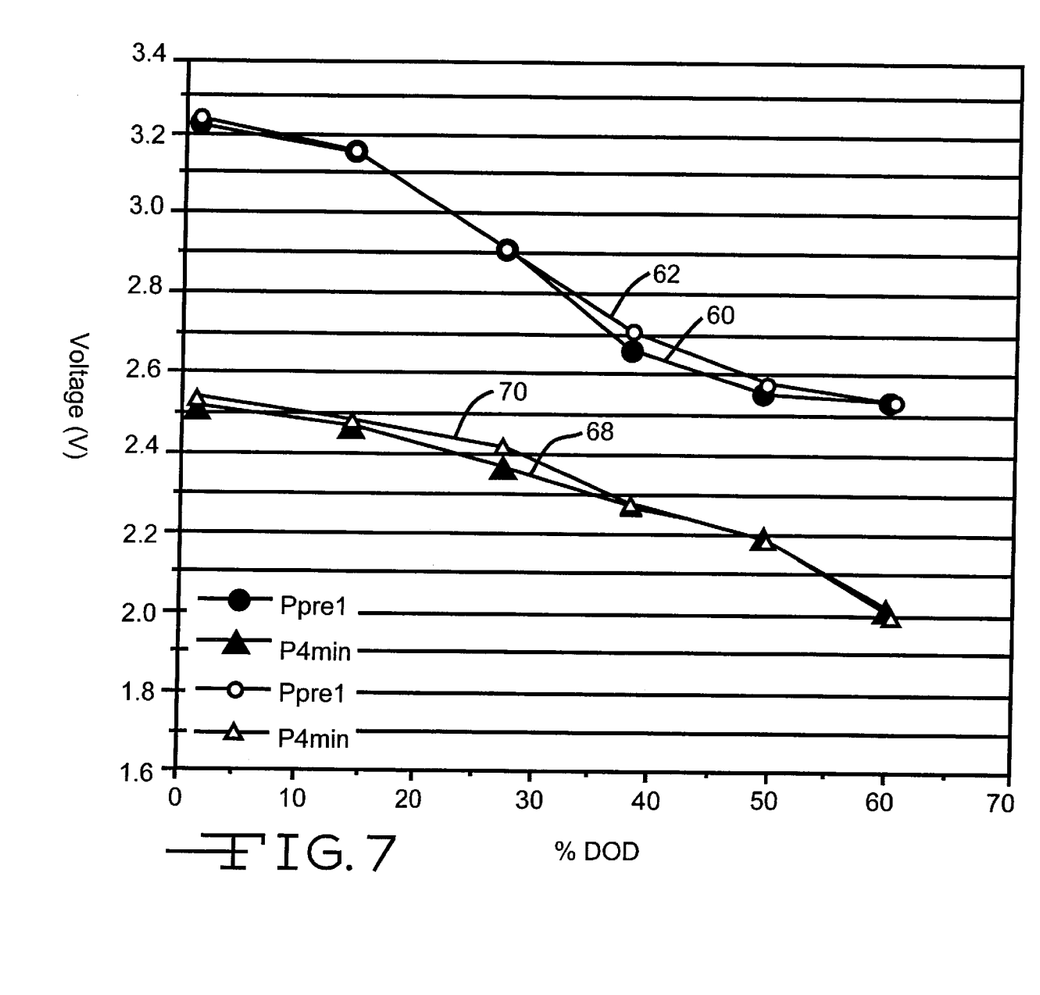
FIG. 7 is a graph constructed from a comparison of the average prepulse voltages and pulse 4 minimum voltages for the two cell groups used to construct the graph of FIG. 6.

Nine cells were constructed in a similar manner as described in Example II except for the stoichiometry of the SVO material. In particular, five cells were built having ε-SVO with stoichiometry formula of $Ag_2V_4O_{11}$ (group 3) and four cells were constructed having a mixture of γ-SVO (45% mole) and ε-SVO (55% mole) with stoichiometry formula of $Ag_{1.82}V_4O_{10.91}$ (group 4). After burn-in and acceptance pulse train discharge, these cells were discharged under a 16.5 kΩ load interrupted every 60 days by pulse trains consisting of four 10 second pulses having a cathode current density of 22.2 mA/cm$^2$ with a 15 second rest between pulses. The average pulse train data from the initial 6 pulse trains is summarized in FIG. 6 (P1min. comparison) and in FIG. 7 (P4min. comparison). In particular, curves 60 and 62 in FIGS. 6 and 7 are the respective prepulse voltages for the groups 3 and 4 cells, curves 64 and 66 in FIG. 6 are of the pulse 1 minimum voltages and curves 68 and 70 in FIG. 7 are of the pulse 4 minimum voltages of the respective groups 3 and 4 cells.

This data clearly shows three discharge regions. For the group 3 cells with a cathode stoichiometry of $Ag_2V_4O_{11}$, three discharge regions were identified. They are: region 1 from 0% to about 22.7% DOD; region 2 from about 22.7% to about 45% DOD; and region 3 from about 45% to 100% DOD. For the group 4 cells having a cathode stoichiometry of $Ag_{1.82}V_4O_{10.91}$, three discharge regions were identified. They are: region 1 from 0% to about 22.7%; region 2 from about 22.7% to about 48% DOD; and region 3 from about 48% to 100% DOD. This data shows that in region 2 discharge, the group 4 cells presented higher or equal pulse minimum potentials than that of the group 3 cells. Equal or larger values of (V×I) are expected from the group 4 cells relative to that of the group 1 cells. Thus, in the cells with a sandwiched cathode design of SVO-screen-$CF_x$-screen-SVO, it is also preferable to use a mixture of γ-phase SVO and ε-phase SVO as the SVO cathode active mixture over that of pure ε-phase SVO. The mixed phase SVO has a stoichiometry formula of $Ag_xV_4O_y$ where $1.6<x<2.0$ and $10.8<y<11.0$.

It is appreciated that various modifications to the inventive concepts described herein may be apparent to these of ordinary skill in the art without departing from the spirit and scope of the present invention as defined by the appended claims.

What is claimed is:

1. An electrochemical cell, which comprises:
    a) an anode of an alkali metal;
    b) a cathode of a configuration: first SVO/current collector/$CF_x$/current collector/second SVO, wherein the first and second SVO materials are of the general formula $Ag_xV_2O_y$ with $0.80 \leq x<1.0$ and $5.4 \leq y<5.5$; and
    c) a nonaqueous electrolyte activating the anode and the cathode.

2. The electrochemical cell of claim 1 wherein the first and second SVO materials are γ-SVO having in the general formula x=0.80 and y=5.4.

3. The electrochemical cell of claim 1 wherein the first and second SVO materials are a mixture of γ-SVO having in the general formula x=0.80 and y=5.4 and ε-SVO having in the general formula x=1.0 and y=5.5.

4. The electrochemical cell of claim 1 wherein the first and second SVO materials comprise 45% mole of γ-SVO having in the general formula x=0.80 and y=5.4 and 55% mole of ε-SVO having in the general formula x=1.0 and y=5.5.

5. The electrochemical cell of claim 1 wherein the current collectors are selected from the group consisting of stainless steel, titanium, tantalum, platinum, gold, aluminum, cobalt nickel alloys, nickel-containing alloys, highly alloyed ferritic stainless steel containing molybdenum and chromium, and nickel-, chromium-, and molybdenum-containing alloys.

6. The electrochemical cell of claim 1 wherein the current collectors are titanium having a coating selected from the group consisting of graphite/carbon material, iridium, iridium oxide and platinum provided thereon.

7. The electrochemical cell of claim 1 wherein the anode is lithium, the first and second SVO materials are a mixture of γ-SVO having in the general formula x=0.80 and y=5.4 and ε-SVO having in the general formula x=1.0 and y=5.5, and the current collectors are of titanium.

8. The electrochemical cell of claim 1 wherein the anode is comprised of lithium.

9. The electrochemical cell of claim 1 wherein the SVO materials and the $CF_x$ material comprises from about 80 weight percent to about 99 weight percent of the respective active materials.

10. The electrochemical cell of claim 9 wherein at least one of the SVO materials and the $CF_x$ material further comprises a binder material and a conductive additive.

11. The electrochemical cell of claim 10 wherein the binder material is a fluoro-resin powder.

12. The electrochemical cell of claim 10 wherein the conductive additive is selected from the group consisting of carbon, graphite powder, acetylene black, nickel powder, aluminum powder, titanium powder, stainless steel powder, and mixtures thereof.

13. The electrochemical cell of claim 1 wherein at least one of the SVO materials and the $CF_x$ material comprises about 0 to 3 weight percent of a conductive additive, about 1 to 5 weight percent of a fluoro-resin powder and about 94 to 99 weight percent of the respective active materials.

14. The electrochemical cell of claim 1 wherein the electrolyte has a first solvent selected from an ester, a linear ether, a cyclic ether, a dialkyl carbonate, and mixtures thereof, and a second solvent selected from a cyclic carbonate, a cyclic ester, a cyclic amide, and mixtures thereof.

15. The electrochemical cell of claim 14 wherein the first solvent is selected from the group consisting of tetrahydrofuran (THF), methyl acetate (MA), diglyme, triglyme, tetragylme, dimethyl carbonate (DMC), 1,2-dimethoxyethane (DME), 1,2-diethoxyethane (DEE), 1-ethoxy,2-methoxyethane (EME), ethyl methyl carbonate, methyl propyl carbonate, ethyl propyl carbonate, diethyl carbonate, dipropyl carbonate, and mixtures thereof, and the second solvent is selected from the group consisting of propylene carbonate (PC), ethylene carbonate (EC), butylene carbonate, acetonitrile, dimethyl sulfoxide, dimethyl, formamide, dimethyl acetamide, γ-valerolactone, γ-butyrolactone (GBL), N-methyl-pyrrolidinone (NMP), and mixtures thereof.

16. The electrochemical cell of claim 1 wherein the electrolyte includes a lithium salt selected from the group consisting of $LiPF_6$, $LiBF_4$, $LiAsF_6$, $LiSbF_6$, $LiClO_4$, $LiAlCl_4$, $LiGaCl_4$, $LiC(SO_2CF_3)_3$, $LiN(SO_2CF_3)_2$, LiSCN, $LiO_3SCF_3$, $LiC_6F_5SO_3$, $LiO_2CCF_3$, $LiSO_6F$, $LiB(C_6H_5)_4$, $LiCF_3SO_3$, and mixtures thereof.

17. The electrochemical cell of claim 1 wherein the electrolyte is 0.8M to 1.5M $LiAsF_6$ or $LiPF_6$ dissolved in a 50:50 mixture, by volume, of propylene carbonate and 1,2-dimethoxyethane.

18. An electrochemical cell, which comprises:

a) an anode of lithium;

b) a cathode of a configuration: first SVO/titanium current collector/$CF_x$/titanium current collector/second SVO, wherein the first and second SVO materials are of the general formula $Ag_xV_2O_y$ with $0.80 \leq x < 1.0$ and $5.4 \leq y < 5.5$; and c) a nonaqueous electrolyte.

* * * * *

UNITED STATES PATENT AND TRADEMARK OFFICE
CERTIFICATE OF CORRECTION

PATENT NO. : 6,607,861 B2
DATED : August 19, 2003
INVENTOR(S) : Hong Gan et al.

It is certified that error appears in the above-identified patent and that said Letters Patent is hereby corrected as shown below:

<u>Title page,</u>
Item [*] Notice, should read as follows:
-- [*] Notice: Subject to any disclaimer, the term of this patent is extended or adjusted under 35 U.S.C. 154(b) by 166 days. --.

Signed and Sealed this

Seventeenth Day of February, 2004

JON W. DUDAS
*Acting Director of the United States Patent and Trademark Office*